US008207341B2

(12) United States Patent
Springfield et al.

(10) Patent No.: US 8,207,341 B2
(45) Date of Patent: Jun. 26, 2012

(54) PROCESS OR SYNTHESIZING SUBSTITUTED ISOQUINOLINES

(75) Inventors: Shawn A. Springfield, Allentown, NJ (US); Wendel W. Doubleday, Doylestown, PA (US); Percy Sarwood Manchand, Montclair, NJ (US); Hyungcheol Kim, Daejeon (KR); Sangsoo Lee, Daejeon (KR); Chunyoung Kim, Daejeon (KR); Soonha Yang, Daejeon (KR); Eunhee Choi, Seoul (KR)

(73) Assignee: Bristol-Myers Squibb Company, Princeton, NJ (US)

( * ) Notice: Subject to any disclaimer, the term of this patent is extended or adjusted under 35 U.S.C. 154(b) by 368 days.

(21) Appl. No.: 12/547,158

(22) Filed: Aug. 25, 2009

(65) Prior Publication Data
US 2010/0056792 A1 Mar. 4, 2010

Related U.S. Application Data

(60) Provisional application No. 61/094,088, filed on Sep. 4, 2008.

(51) Int. Cl.
C07D 217/24 (2006.01)
(52) U.S. Cl. ...................................... 546/141
(58) Field of Classification Search ........................ None
See application file for complete search history.

(56) References Cited

U.S. PATENT DOCUMENTS

| 5,223,432 | A | 6/1993 | Wirz et al. |
|---|---|---|---|
| 7,449,479 | B2 | 11/2008 | Wang et al. |
| 7,582,605 | B2 | 9/2009 | Moore et al. |
| 7,601,709 | B2 | 10/2009 | Miao et al. |
| 7,605,126 | B2 | 10/2009 | Niu et al. |
| 7,635,683 | B2 | 12/2009 | Gai et al. |
| 2005/0209135 | A1 | 9/2005 | Busacca et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0181868 | A1 | 7/2008 | Sun et al. |
| 2008/0279821 | A1 | 11/2008 | Niu et al. |
| 2009/0274656 | A1 | 11/2009 | Wang et al. |

FOREIGN PATENT DOCUMENTS

| WO | WO 98/17679 | 4/1998 |
|---|---|---|
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |

(Continued)

OTHER PUBLICATIONS

Briet et al, Tetrahedron, 58 (2002), pp. 5761-5766.* U.S. Appl. No. 12/559,179, filed Sep. 14, 2009, Hiebert et al.
U.S. Appl. No. 12/566,286, filed Sep. 24, 2009, Wang et al.
U.S. Appl. No. 12/566,441, filed Sep. 24, 2009, Hiebert et al.
U.S. Appl. No. 12/628,248, filed Dec. 1, 2009, Hiebert et al.
U.S. Appl. No. 12/635,144, filed Dec. 10, 2009, Wang et al.
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

(Continued)

Primary Examiner — Zinna Northington Davis
(74) Attorney, Agent, or Firm — Pamela A. Mingo

(57) ABSTRACT

The present disclosure generally relates to a process for synthesizing optionally substituted 1-chloro-4-methoxyisoquinolines. The present disclosure also relates to intermediates useful in this process.

12 Claims, No Drawings

FOREIGN PATENT DOCUMENTS

| | | |
|---|---|---|
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005690 | 1/2009 |
| WO | WO 2009/010804 | 1/2009 |
| WO | WO 2009/014730 | 1/2009 |
| WO | WO 2009/082701 | 7/2009 |
| WO | WO 2009/085659 | 7/2009 |
| WO | WO 2009/129109 | 10/2009 |
| WO | WO 2009/140475 | 11/2009 |
| WO | WO 2009/140500 | 11/2009 |
| WO | WO 2009/142842 | 11/2009 |
| WO | WO 2009/146347 | 12/2009 |
| WO | WO 2009/148923 | 12/2009 |

OTHER PUBLICATIONS

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalie Acid", Synthesis, pp. 365-366 (1992).

* cited by examiner

PROCESS OR SYNTHESIZING SUBSTITUTED ISOQUINOLINES

CROSS-REFERENCE TO RELATED APPLICATIONS

This application claims the benefit of U.S. Provisional Application Ser. No. 61/094,088 filed Sep. 4, 2008.

The present disclosure generally relates to a process for synthesizing optionally substituted 1-chloro-4-methoxyisoquinolines. The present disclosure also relates to intermediates useful in this process.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40 percent of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

Compound (II) is an intermediate in the preparation of compound (III) which has demonstrated activity against Hepatitis C.

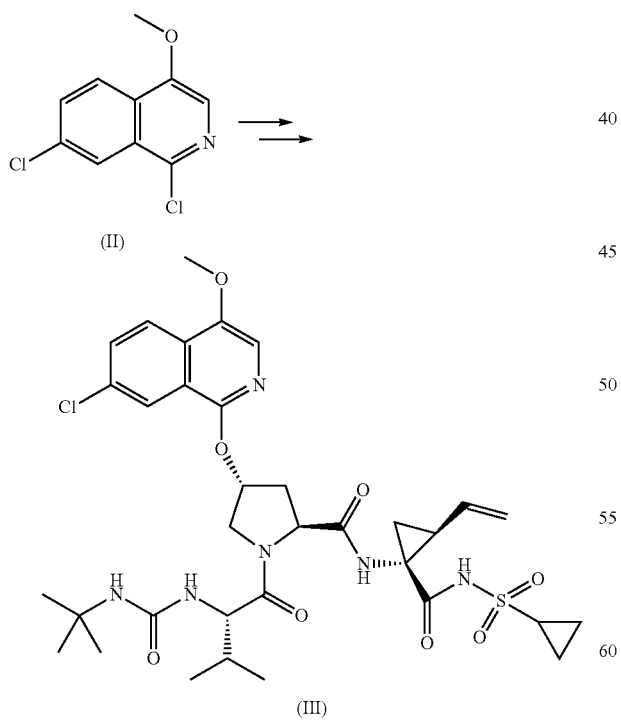

For purposes of large-scale production there is a need for a high-yielding synthesis of compound (II) and related analogs that is both efficient and cost-effective.

In a first aspect the present disclosure provides a process for preparing a compound of formula (I)

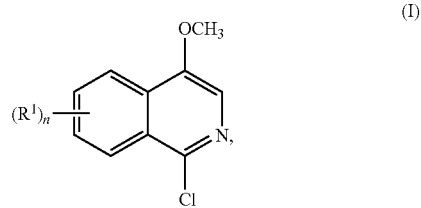

the process comprising:
(a) treating a compound of formula (A)

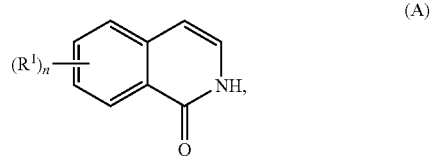

wherein
n is 0, 1, 2, 3, or 4; and
each $R^1$ is independently selected from alkoxy, alkyl, amino, aryl, cyano, halo, haloalkoxy, mercapto, and nitro;
with an anhydrous acid in the presence of methanol and a hypervalent iodine oxidizing agent; and
(b) treating the compound of step (a) with a chlorinating agent.

In a first embodiment of the first aspect, n is 1; and $R^1$ is halo.

In a second embodiment of the first aspect the acid of step (a) is methanesulfonic acid.

In a third embodiment the hypervalent iodine oxidizing agent is selected from phenyl iodine diacetate, bis(4-methylbenzenesulfonato-κO)phenyliodine, bis(2,2-dimethylpropanoato-κO)phenyliodine, phenylbis(trichloroacetato-O)iodine, bis(benzoato-κO)phenyliodine, phenylbis(2,2,2,-trifluoroacetateo-KO)iodine, and dichloroiodobenzene. In a fourth embodiment the hypervalent iodine oxidizing agent is phenyl iodine diacetate.

In a fifth embodiment of the first aspect, the chlorinating agent of step (b) is selected from $POCl_3$ and $PCl_5$. In a sixth embodiment the chlorinating agent is $POCl_3$.

In a seventh embodiment of the first aspect, the process further comprises a process for preparing a compound of formula (A)

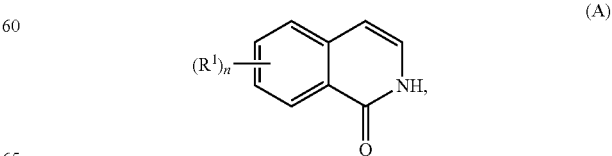

the process comprising:
(a) treating a compound of formula (B)

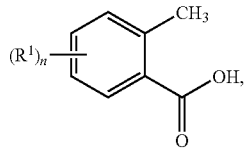

(B)

with oxalyl chloride and ammonium hydroxide;
(b) treating the product of step (a) with N,N-dimethylformamide dimethyl acetal; and
(c) treating the product of step (b) with a base.
In an eighth embodiment, n is 1; and $R^1$ is halo.
In a ninth embodiment the base of step (c) is selected from potassium tert-butoxide, potassium tert-amylate, and potassium hexamethyldisilazide. In an eighth embodiment the base is potassium tert-amylate.
In a tenth embodiment of the first aspect the process for preparing compound (A) is continuous.
In a second aspect the present disclosure provides a process for preparing a compound of formula (I)

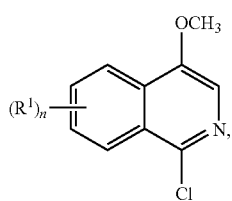

(I)

wherein
n is 0, 1, 2, 3, or 4; and
each $R^1$ is independently selected from alkoxy, alkyl, amino, aryl, cyano, halo, haloalkoxy, mercapto, and nitro; the process comprising:
(a) treating a compound of formula (C)

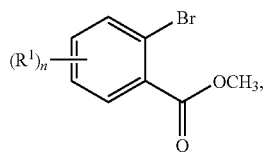

(C)

with n-butyl vinyl ether in the presence of a palladium catalytic system;
(b) treating the product of step (a) with a strong acid in the presence of water;
(c) treating the product of step (b) with a brominating agent to provide a compound of formula (D)

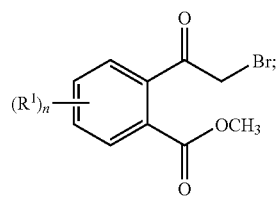

(D)

(d) treating the compound of formula (D) with diformylamide in the presence of a phase transfer catalyst then treating the resulting mixture with methanol to provide a compound of formula (E)

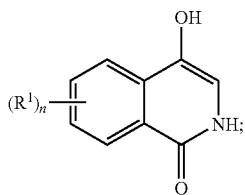

(E)

(e) subjecting the compound of formula (E) to methoxylating or methylating conditions to form a compound of formula (F)

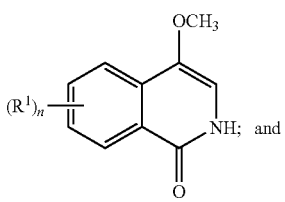

(F)

and (f) treating the compound of formula (F) with a chlorinating agent.

In a first embodiment of the second aspect the palladium catalytic system of (a) is selected from palladium acetate with tri-o-tolylphosphine and diisopropylethylamine and palladium acetate with triphenylphosphine and diisopropylethylamine. In a second embodiment the palladium catalytic system is palladium acetate with tri-o-tolylphosphine and diisopropylethylamine.

In a third embodiment of the second aspect the strong acid in step (b) is $H_3PO_4$.

In a fourth embodiment of the second aspect the brominating agent in step (c) is selected from bromine and N-bromosuccinimide. In a fifth embodiment the brominating agent is bromine.

In a sixth embodiment of the second aspect the phase transfer catalyst of step (d) is tetrabutylammonium bromide.

In a seventh embodiment of the second aspect the compound of formula (E) in step (e) is subjected to methylating conditions. In an eighth embodiment the methylating conditions comprise treating the compound of formula (E) with dimethyl sulfate in the presence of a base.

In a ninth embodiment of the second aspect the compound of formula (E) in step (e) is subjected to methoxylating conditions. In a tenth embodiment the methoxylating conditions comprise treating the compound of formula (E) with methanolic hydrochloric acid in dioxane. In an eleventh embodiment the methoxylating conditions comprise treating the compound of formula (E) with methanesulfonic acid in methanol.

In a twelfth embodiment of the second aspect the chlorinating agent of step (f) is selected from $POCl_3$ and $PCl_5$. In a thirteenth embodiment the chlorinating agent is $POCl_3$.

In a fourteenth embodiment of the second aspect n is 1; and $R^1$ is halo.

In a third aspect the present disclosure provides a process for preparing a compound of formula (F)

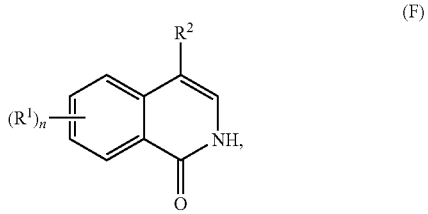
(F)

the process comprising:
(a) treating a compound of formula (A)

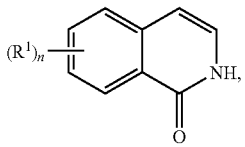
(A)

wherein
n is 0, 1, 2, 3, or 4; and
each $R^1$ is independently selected from alkoxy, alkyl, amino, aryl, cyano, halo, haloalkoxy, mercapto, and nitro;
with an anhydrous acid in the presence of $R^3XH$ and a hypervalent iodine oxidizing agent; wherein
X is selected from S, O, and $NR^4$;
$R^3$ is selected from alkyl, aryl, and arylalkyl; and
$R^4$ is selected from hydrogen and alkyl.

In a first embodiment of the first aspect the hypervalent iodine oxidizing agent is selected from phenyl iodine diacetate, bis(4-methylbenzenesulfonato-κO)phenyliodine, bis(2,2-dimethylpropanoato-κO)phenyliodine, phenylbis(trichloroacetato-0)iodine, bis(benzoato-κO)phenyliodine, phenylbis(2,2,2,-trifluoroacetateo-KO)iodine, and dichloroiodobenzene. In a second embodiment the hypervalent iodine oxidizing agent is phenyl iodine diacetate.

In a third embodiment of the first aspect
n is 1;
$R^1$ is halo; and
$R^2$ is alkoxy wherein the alkoxy is methoxy.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

As used in the present specification, the following terms have the meanings indicated:

The term "acid," as used herein, refers to a reagent capable of donating a proton during the course of a reaction. Examples of acids include strong acids such as $H_2SO_4$, $H_3PO_4$, $HNO_3$, and HCl and weak acids such as acetic acid and benzoic acid.

The term "alkoxy," as used herein, refers to an alkyl group attached to the parent molecular moiety through an oxygen atom.

The term "alkyl," as used herein, refers to a group derived from a straight or branched chain saturated hydrocarbon containing from one to six carbon atoms.

The term "amino," as used herein, refers to $-NH_2$.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl.

The term "arylalkyl," as used herein, refers to an alkyl group substituted by one, two, or three aryl groups.

The term "base," as used herein, refers to a reagent capable of accepting protons during the course of a reaction without acting as a nucleophile in the reaction. Examples of bases include alkoxides such as potassium tert-butoxide, sodium tert-butoxide, potassium tert-amylate, sodium tert-amylate; disilylamides such as lithium hexamethyldisilazide and potassium hexamethyldisilazide; non-nucleophilic amines such as triethylamine, diisopropylethylamine, and diisopropylamine; heterocyclic amines such as imidazole, pyridine, pyridazine, and pyrimidine; and bicyclic amines such as DBN (1,5-diazabicyclo[4.3.0]non-5-ene) and DBU (1,8-diazabicyclo[5.4.0]undec-7-ene. The base chosen for a particular conversion depends on the nature of the starting materials, the solvent or solvents in which the reaction is conducted, and the temperature at which the reaction is conducted.

The term "brominating agent," as used herein, refers to an agent capable of replacing a particular group on a molecule with a bromine atom. In the present disclosure the brominating agent is used to replace alpha-keto hydrogen atom with a bromine atom to generate an alpha-halo ketone. Representative brominating agents include $Br_2$, NBS, and $CBr_4$.

The term "chlorinating agent," as used herein, refers to an agent capable of replacing a particular group on a molecule with a chlorine atom. In the present disclosure the chlorinating agent is used to replace an enolic hydroxy group with a chlorine atom to generate a vinyl chloride. Representative chlorinating agents include $POCl_3$, $PCl_5$, and $PCl_3$.

The term "cyano," as used herein, refers to —CN.

The terms "halo" and "halide," as used herein, refer to F, Cl, Br, or I.

The term "haloalkoxy," as used herein, refers to a haloalkyl group attached to the parent molecular moiety through an oxygen atom.

The term "mercapto," as used herein, refers to —SH.

The term "nitro," as used herein, refers to $-NO_2$.

The term "palladium catalytic system," as used herein, refers to a palladium catalyst and the necessary ligands and/or base required for the catalyst to react. Representative palladium catalytic systems include tetrakistriphenylphosphine palladium; palladium acetate with tri-o-tolylphosphine and diisopropylethylamine; and palladium acetate with triphenylphosphine and diisopropylethylamine.

The term "phase transfer catalyst," as used herein refers to a catalyst which facilitates the migration of a reactant in a heterogeneous system from one phase into another phase where reaction can take place. Representative phase transfer catalysts include hexadecyltributylphosphonium bromide, methyltrioctylammonium chloride, and tetrabutylammonium bromide.

The term "methoxylating conditions," as used herein, refers to conditions that replace an enolic hydroxy group with a methoxy group to form an enol ether. Representative methoxylating conditions include methanolic hydrochloric acid in dioxane and methanesulfonic acid in methanol.

The term "methylating conditions," as used herein, refers to conditions that replace the hydrogen of a hydroxy group with a methyl group. Representative methylating conditions include dimethyl sulfate in the presence of a base and methyl iodide treatment following deprotonation with a base.

The term "treating," as used herein, refers to contacting a substrate with one or more reagents and/or additional substrates. The reagents and/or additional substrates may be added to the initial substrate or, alternatively, the initial substrate may be added to the reagents and/or additional substrates.

All of the processes in the present disclosure can be conducted as continuous processes. The term "continuous process," as used herein, represents steps conducted without isolation of the intermediate.

Starting materials can be obtained from commercial sources or prepared by well-established literature methods known to those of ordinary skill in the art. It will be readily apparent to one of ordinary skill in the art that compounds of formula (I) can be synthesized by substitution of the appropriate reactants and agents in the syntheses shown below. It will also be readily apparent to one skilled in the art that the specific reaction conditions, such as solvents and temperatures, can vary depending on the nature of the variables to successfully complete the syntheses below.

Scheme 1 shows one method of synthesizing compounds of formula (I). Compounds of formula (B) can be converted to compounds of formula (B') by treatment with oxalyl chloride followed by ammonium hydroxide. Conversion of compounds of formula (B') can be converted to compounds of formula (A) via treatment with N,N-dimethylformamide dimethyl acetal followed by treatment with a base. Examples of bases used in this reaction include potassium tert-amylate, potassium tert-butoxide, and potassium hexamethyldisilazide.

Compounds of formula (A) can be converted to compounds of formula (F) by treatment with an anhydrous acid in the presence of methanol and a hypervalent iodine oxidizing agent such as phenyl iodine diacetate, bis(4-methylbenzenesulfonato-κO)phenyliodine, bis(2,2-dimethylpropanoato-κO)phenyliodine, phenylbis(trichloroacetato-O)iodine, bis(benzoato-κO)phenyliodine, phenylbis(2,2,2,-trifluoroacetateo-KO)iodine, ordichloroiodobenzene. Compounds of formula (F) can in turn be converted to compounds of formula (I) by treatment with a chlorinating agent such as $POCl_3$ or $PCl_5$.

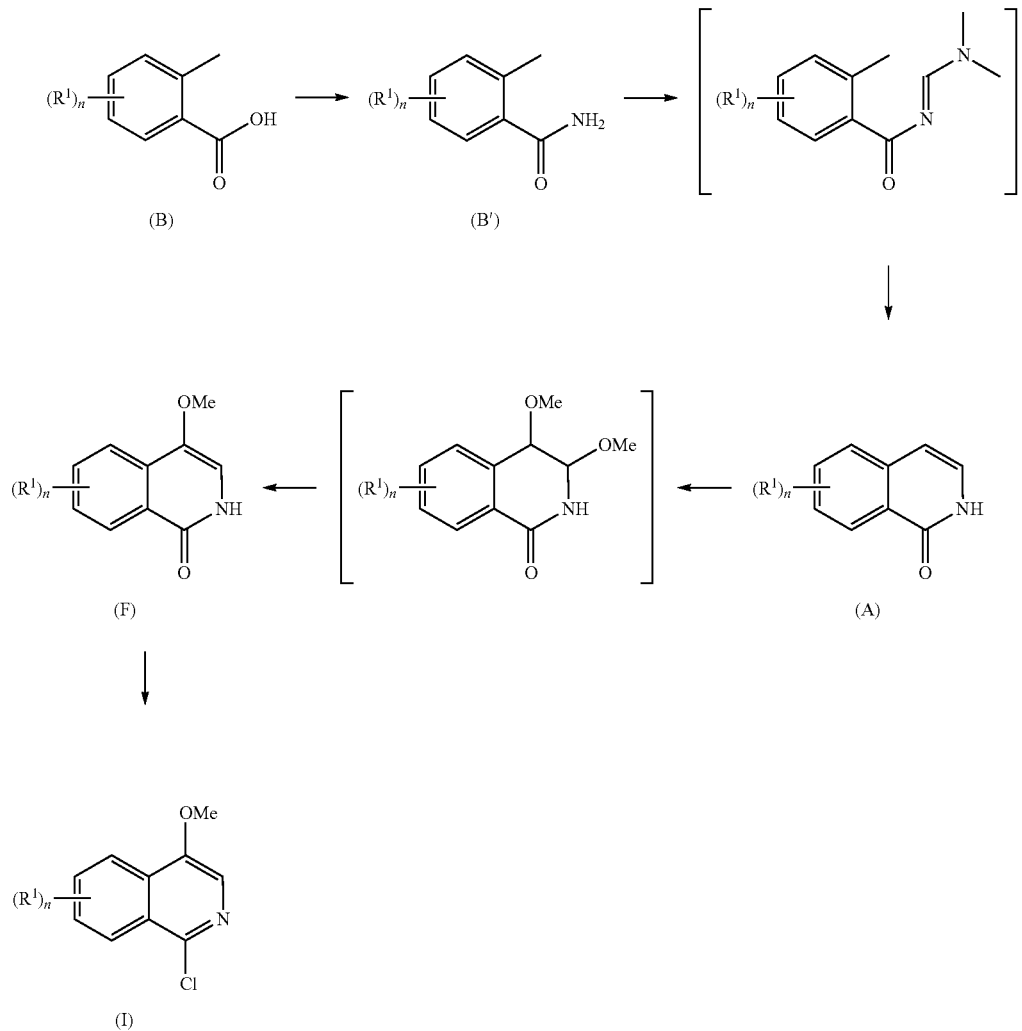

Scheme 2

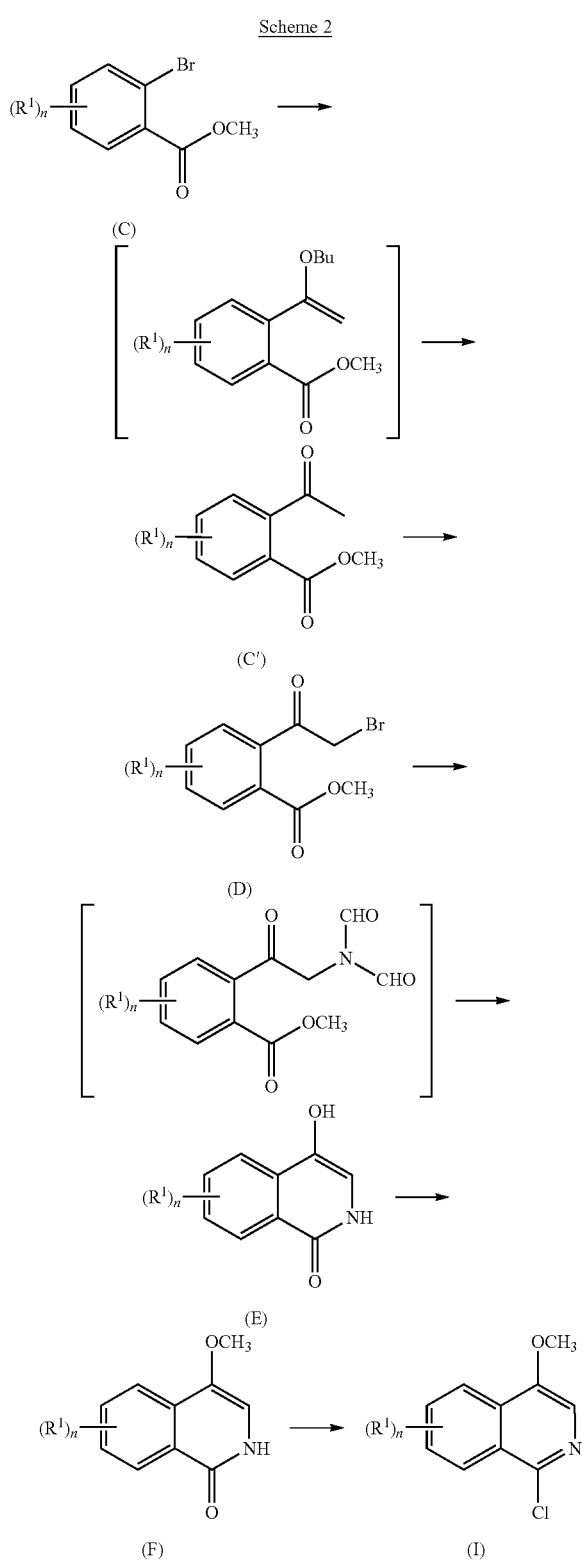

An alternative synthesis of compounds of formula (I) is shown in Scheme 2. Compounds of formula (C) can be converted to compounds of formula (C') by treatment with n-butyl vinyl ether in the presence of a palladium catalytic system, followed by treatment with a strong acid in the presence of water. Examples of palladium catalytic systems include palladium acetate with tri-o-tolylphosphine and diisopropylethylamine and palladium acetate with triphenylphosphine and diisopropylethylamine. Representative strong acids include $H_3PO_4$, $H_2SO_4$, and HCl. In one embodiment the strong acid is $H_3PO_4$.

Compounds of formula (C') can be converted to compounds of formula (D) by treatment with a brominating agent. Examples of brominating agents include bromine and N-bromosuccinimide.

Conversion of compounds of formula (D) to compounds of formula (E) can be accomplished by treatment with diformylamide in the presence of a phase transfer catalyst and subsequent treatment with methanol. In one embodiment the phase transfer catalyst is tetrabutylammonium bromide.

Compounds of formula (E) can be converted to compounds of formula (F) by subjecting the starting vinyl hydroxide to either methoxylating or methylating conditions. One example of methylating conditions is treatment of the compound of formula (E) with dimethyl sulfate in the presence of a base. Examples of methoxylating conditions include treatment of the vinyl hydroxide with methanolic hydrochloric acid in dioxane and treatment with methanesulfonic acid in methanol.

Conversion of compounds of formula (F) to compounds of formula (I) can be accomplished using chlorinating conditions as described above.

EXAMPLES

The following non-limiting examples are illustrative of the disclosure.

Example 1

| Name | grams |
| --- | --- |
| 5-chloro-2-methylbenzoic acid | 20.00 |
| Oxalyl Chloride | 14.88 |
| Dimethylformamide | 0.21 |
| Ammonium Hydroxide | 96.50 |
| 2-Methyltetrahydrofuran | 171.76 |
| 2-Methyltetrahydrofuran-biphasic quench | 85.88 |
| Water-MeTHF wash | 100.00 |

To a 500 ml, 3-neck round-bottom (flask A) equipped with a stir bar, nitrogen inlet and temperature probe were charged the following reagents respectively:
1) 5-chloro-2-methylbenzoic acid
2) MeTHF---> homogeneous solution
3) DMF
4) Oxalyl chloride addition over four minutes The reaction was allowed to stand for ~1 hr at room temperature at which time LC analysis (quenched aliquot in MeOH) indicated >99.5% conversion of starting material;

In a separate flask (Flask B) MeTHF and 5N $NH_4OH$ were combined and stirred vigorously at room temperature.

The slightly turbid reaction solution in Flask A was then transferred to an addition funnel and added dropwise to flask B over approximately 7 minutes.

Upon complete addition, the biphasic solution was stirred an additional 10 min prior to transferring the total contents of Flask B to a separatory funnel.

The layers were then separated and the remaining organic layer was washed 1×100 ml H₂O.

Layers were then split and assayed.

Example 2

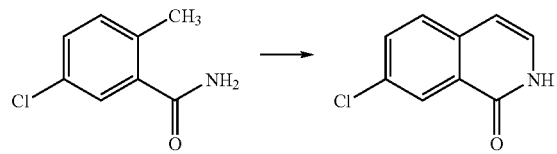

| Name | grams |
|---|---|
| Starting amide | 19.58 |
| Methanamine, 1,1-Dimethoxy-N,N-dimethyl- | 15.13 |
| Potassium-t-amylate | 122.42 |
| Toluene | 341.16 |
| N-Methylpyrrolidone | 151.11 |
| Water | 146.85 |
| Hydrogen Chloride | 23.89 |
| Heptane | 66.92 |
| Methanol | 7.77 |

The above solution of 5-chloro-2-methylbenzamide was atmospherically solvent switched to toluene.

The resulting solution was then cooled to 50° C.

DMF/DMA was charged to the reaction solution.

Heated to reflux.

The solution was allowed to reflux for ~3 hrs in order to convert all of the 5-Cl-2-methyl benzamide to the desired amidine intermediate.

Removal of the methanol byproduct was then performed by distillation.

The resulting warm, homogeneous solution was then inversely added to a separate reactor that contained 25 wt % potassium t-amylate/toluene solution pre-heated to 85° C. Addition rate was maintained ≦12 L/min on scale.

Upon complete addition, heating was maintained of the now heterogeneous solution until complete conversion of the amidine intermediate was observed.

The reaction was then cooled to ~50° C.

Methanol was added, the solution remained heterogeneous.

Began vacuum distillation (volume reduction involves removing 2-methyl-2-butanol and toluene) to an approximate concentration of 10 ml/g.

Temperature was reduced to room temperature, then n-heptane was added to the heterogeneous solution.

A pre-made solution of 50:50 NMP/H₂O was then quickly added via addition funnel.

The resulting bi-phasic solution was then stirred for ~10 minutes prior to transferring to a separatory funnel.

The layers separated quickly and cleanly.

The aqueous NMP layer was cut and transferred to a separate 1L 3-neck round-bottom equipped with a mechanical stirrer, nitrogen inlet and temperature probe.

While stirring, acid was added via addition funnel in order to neutralize the reaction and subsequently precipitate desired product from solution.

A total of 100 ml H₂O was then added dropwise to the resulting slurry.

The heterogeneous solution was stirred at room temperature for one hour prior to filtering.

The resulting cake was washed with 100 ml of 20% NMP/H₂O, then 3×100 ml H₂O.

The cake was dried on the frit for several hours under vacuum prior to being transferred to the vacuum oven to continue drying overnight @ 30" Hg and 50° C. Typical results provide 89% isolated yield with ≧98% LCAP (250 nm wavelength).

Example 3

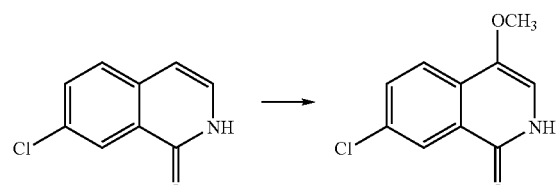

| Name | equiv | grams |
|---|---|---|
| Starting | 1.00 | 15.00 |
| Iodosobenzene Diacetate | 1.10 | 30.19 |
| Methanesulfonic Acid | 1.00 | 8.05 |
| Methanol | 88.75 | 237.51 |

To a 500 ml, 3-neck round-bottom flask (Flask A) equipped with overhead stirring, nitrogen inlet, heating mantle and temperature probe were charged the following reagents respectively:
1) starting isocarbostyril
2) Methanol (10 ml/g-bulk-LR)
3) Methanesulfonic acid Cooled Flask A via ice bath to ~0° C.

In a separate 250 ml, 3-neck round-bottom flask (Flask B) equipped with stir bar, nitrogen inlet, temperature probe and heating mantle was dissolved the oxidant in methanol (10 ml/g-bulk-LR) at 30° C.

The completely homogeneous oxidant solution was then transferred to an addition funnel and added dropwise to the contents of Flask A, which resulted in a homogeneous solution.

The ice bath was removed and the reaction was allowed to age at room temperature for ~1 hour prior to heating to reflux.

The reaction was then aged at reflux until complete conversion was observed (3-5 hours).

Upon complete conversion the reaction volume was then reduced via atmospheric distillation (collected ~92 ml distillate).

The reaction was then cooled to room temperature and the resulting slurry was aged @ rt overnight.

The following morning, a total of 45 ml of H₂O was slowly added dropwise via addition funnel as anti-solvent.

The resulting slurry was aged ~1 hour at room temperature prior to filtering.

The resulting cake was washed with 100 ml 50:50 H₂O/MeOH, then 2×100 ml H₂O.

The solids were dried on the frit under vacuum for several hours prior to being transferred to the vac oven were they continued to dry @ 50° C. and 30" Hg over the weekend. Typical results range from 75-85% isolated yield with ≧97 LCAP (250 nm wavelength).

Example 4

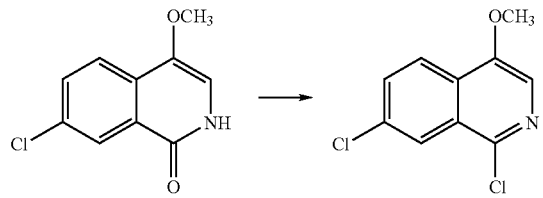

| Name | equiv | grams |
|---|---|---|
| Starting isocarbostyril | 1.00 | 10.00 |
| Phosphoryl Chloride | 3.00 | 21.94 |
| Acetonitrile | n/a | 39.16 |
| Water-inverse quench | n/a | 200.00 |
| Potassium Phosphate, Tribasic, N-Hydrate | | 100.24 |
| Tetrahydrofuran | | 101.90 |
| Toluene | | 30.49 |
| Tetrahydrofuran-Carbon cake wash | | 49.62 |
| Heptane-solvent switch and cake wash | | 314.46 |

To a 250 ml 3-neck round-bottom flask (Flask A) equipped with a stir bar, nitrogen inlet, temperature probe, heating mantle and reflux condenser were charged the following reagents respectively:
1) starting isocarbostyril
2) acetonitrile
3) POCl₃ (maintained temperature during addition below 30° C.)

Began heating to reflux and followed conversion by LC analysis.

In a separate, 3-neck round-bottom flask (Flask B) equipped with a stir bar, temperature probe, and cooling capabilities were charged the following reagents respectively:
1) water-inverse quench
2) potassium phosphate, tribasic, N-hydrate Upon complete conversion the reaction solution was cooled to room temperature.

The contents of Flask A were then transferred to Flask B maintaining the temperature below 10° C. during the inverse addition.

Upon complete transfer, the resulting slurry was aged between 0-10° C. for 30 minutes.

The following solvents were then charged to begin extractive workup:
1) Tetrahydrofuran
2) Toluene The combined biphasic solution, Vmax=~45 mL/g-bulk-LR, was stirred for 30 minutes as the temperature of the combined mixture increased to room temperature.

Agitation was stopped and the layers were given time to separate.

The layers were split and the aqueous layer was discarded,
The organic layer was subjected to carbon treatment (~10 wt % charge wrt Bulk-LR) for 1 hour with agitation.

MgSO₄ (1:1 charge wrt Bulk-LR) was then charged and the solution was again agitated for 1 hour.

The solids were then filtered off and the resulting cake was washed with Tetrahydrofuran-Carbon cake wash.

Organic layers were then combined and solvent-switched to n-Heptane in order to crystallize product from solution.

After switching to n-Heptane, the resulting slurry is held at 50° C. with agitation for approximately 1 hour prior to cooling to ~7° C.

The resulting 'cold' slurry was then aged with agitation for an additional hour.

The slurry was filtered and the solid washed with n-Heptane.

Typical results range from 77-87% isolated yield; ≧98% LCAP (250 nm wavelength).

Example 5

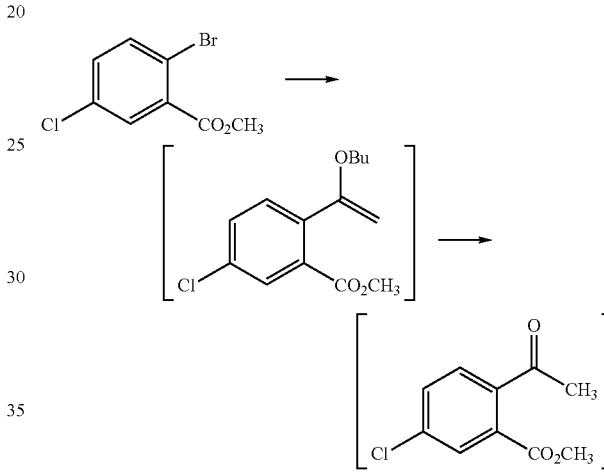

| Name | grams |
|---|---|
| Methyl 2-Bromo-5-chlorobenzoate | 1000.00 |
| Butyl Vinyl Ether | 802.92 |
| Acetonitrile | 3916.50 |
| Pd(OAc)₂ | 27.00 |
| Tri-o-tolylphosphine | 243.99 |
| Diisopropylethylamine | 621.64 |
| Toluene | 4356.00 |
| Water | 1000.00 |
| 5% w/v potassium carbonate | 2000.00 |
| Phosphoric Acid | 3556.00 |
| half-brine aqueous solution | 1000.00 |
| Phosphoric Acid | 1778.00 |
| Toluene | 2178.00 |
| Toluene | 1742.40 |
| Toluene | 871.20 |

HPLC Method for monitoring:
Column Symmetry Shield RP8 3.5 um, 4.6×150 mm
Mobile Phase A: MeOH:H₂O 10:90-0.01 M NH₄OAc,
Mobile Phase B: MeOH:H₂O 90:10-0.01 M NH₄OAc.
Method: 25%, 10 min/100%, 20 min/100%, 220 nm
1. In a 10-L reactor, equipped with a sparging instrument, was placed Methyl 2-Bromo-5-chlorobenzoate (1000 g; 1.00 equiv; 4.01 moles; 1.00 kg) and Acetonitrile (3.92 kg). Purged the colorless solution with Argon for 1 hr at 1 liter per minute (LPM), stirred at 120 RPM.
2. To the degassed solution was added Tri-o-tolylphosphine (243.99 g) to the light suspension was added Diisopropylethylamine (1621.64 g) and Butyl Vinyl Ether (802.92 g). A colorless light suspension was obtained.

3. Sparged the light suspension with Argon for 0.5 hr @ 1 LPM @ 15° C. to minimize loss of volatiles.
4. Under Argon (sparging instrument above surface), to the solution was added Pd(OAc)$_2$ (27.00 g). An orange light suspension was obtained.
5. The solution was heated at 80-82° C. After 1 hour, reaction temp was 48° C.
6. When temperature reached 81° C., HPLC shows about 55 relative area percent to starting material.
7. Stirred under Argon at 80-82° C. for 0.75 hr. A complete conversion was observed.
8. The reaction mixture was stirred under Argon at 80-82° C. for 0.5 more hrs during analysis.
9. Allowed to cool at 35-45° C.
10. Using a 20-L evaporator, the acetonitrile was evaporated to a black oily solid mixture.
11. Added Toluene (2.18 kg) and reevaporate to a black oily solid mixture; large amount of dense solid consisting of diisopropylethylamine hydrobromide and palladium.
12. Added Toluene (4.36 kg).
13. The suspension was stirred at 20-25° C. for 14 hrs. This stirring time favors complete precipitation of the salts.
14. Solids filtered on filter paper. Cake size: 32 cm i.d.×4 cm high, weight not measured.
Cake washed with toluene, 2×1 L; last wash was pale red but showed minimal amount of product. Due to flask volume restriction, washes were concentrated to an oil and added to main solution.

Hydrolysis and Removal of Phosphine

Note: Hydrolysis and extractive process must be done in minimum time. Degradation was observed on prolonged standing at +20,25° C. (RT 12.6 and 12.8 min with HPLC system B) affecting yield and quality.
15. Placed the filtrate in a 22-L 3-neck round-bottom flask placed at +5, 7° C., add gradually Phosphoric Acid (3.56 kg). Addition was done over 30 minutes and temperature allowed to raise at +15, 16° C.
16. Stirred at +15,20° C. for 0.25 hr. HPLC showed a completed reaction (hydrolysis and dissolution of phosphine).
17. Bottom acidic layer separated. Note: Split phase needed to be done at +20,25° C. At lower temperature, separation was long and not efficient.
18. Extracted the acidic layer with toluene, 4× toluene (1.74 kg). Note: Split phase needed to be done at +20,25° C. At lower temperature, separation was long and not efficient. Note: in this reaction, assay of acidic layer after the third extract indicated ca 10% of desired ketone remaining. A fourth extract was performed to lower it below the desired 8%.

| Typical assay in extraction process for a 2-kg run |||||
|---|---|---|---|---|
| Ext | Assay in Toluene || Assay in acidic layer ||
| 1 | 943.8 g | 55.4% | 564.1 g | 33.1% |
| 2 | 205.9 g | 12.1% | 403.6 g | 23.7% |
| 3 | 171.3 g | 10.0% | 246.6 g | 14.5% |
| 4 | 103.8 g | 6.1% | 156.9 g | 9.2% |
| 5 | 60.7 g | 3.6% | 98.4 g | 5.8% |

19. The combined organic layer was washed with a second portion of Phosphoric Acid (1.78 kg) and stirred for 5 min.
20. Bottom acidic layer was separated (10 min). Note: Split phase needed to be done at +20,25° C. At lower temperature, separation was long and not efficient.
21. Acidic layer was extracted with toluene 1× Toluene (871.20 g). Note: Split phase needed to be done at +20,25° C. At lower temperature, separation was long and not efficient.
22. Added combined toluene layer to 5% w/v potassium carbonate (2.00 kg), stirred for 5 minutes, separated.
23. Organic layer was washed with half-brine aqueous solution (1000 g). Note: Aqueous has a final pH 6-8.
24. Toluene solution assayed (average for two samples), Methyl 2-acetyl-5-chlorobenzoate (744.1 g, 3.50 moles; 87.3% yield).
25. Toluene evaporated to remove residual water, orange oil dissolved in Toluene (1.74 kg), filtered to remove residual salt (sodium chloride). Evaporated to an oil using Toluene (1.74 kg) until KF<0.2%.
26. Completed with toluene to a final volume of 10 L (KF=0.006%), and solution containing Methyl 2-acetyl-5-chlorobenzoate (744.1 g; 3.50 moles; 87.3% yield) transferred for further processing.

Typical assay for extractions for a 2-kg run.

|  | Assay (g) | Yield (%) |
|---|---|---|
| Combined organic ext 1-5 | 1598.4 | 93.8 |
| Main H$_3$PO$_4$ layer | 98.4 | 5.8 |
| Wshd organic ext 1-5 | 1477.1 | 86.7 |
| H$_3$PO$_4$ wash | 58.7 | 3.4 |
| H$_3$PO$_4$ wash after extraction | 32.7 | 1.9 |
| Toluene ext of H$_3$PO$_4$ wash | 29.1 | 1.7 |
| Desired product | 1488.1 | 87.3 |

Example 6

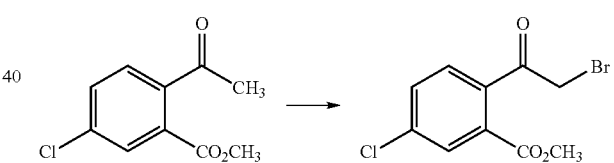

| Name | grams |
|---|---|
| Starting ketone | 1000.00 |
| Bromine | 676.41 |
| Toluene | 8712.00 |
| Bromine | 150.31 |
| Bromine if needed | 75.16 |
| Potassium Carbonate | 649.98 |
| Water | 3000.00 |
| Water | 1500.00 |
| Sodium Chloride (half brine) | 1710.00 |

The solution received contains 1000 g of starting ketone in Toluene.

Notes:

The reaction was followed by GC because the desired product has the same HPLC retention time as the solvent of the reaction (toluene).

Preparation of Solution of Potassium Carbonate and Half Brine should be prepared in advance.

The solution of the starting ketone was transferred to a 20 L reactor and the volume of Toluene was adjusted to give a concentration of ketone of 95 mg/mL-108 mg/mL in Toluene.

Note: If the reaction concentration is higher, formation of Cyclized acetophenone impurity (FW: 180, 5.35 min by GC)

up to 12 Area Percent during the reaction results. The reaction must be done in the specified range to reduce the formation of the impurity.

The reactor was equipped with mechanical stirrer, temperature probe, a condenser, argon inlet and addition funnel.
Notes:
A trap with 4 L of 2N NaOH was used to neutralize HBr formed during the reaction.

An empty flask was placed between the reactor and the Sodium hydroxide trap in case of loss of bromine from the condenser, and to be sure no NaOH went into the reactor.

The solution of starting ketone in the reactor was cooled to between 0° C. and −3.0° C.

Added rapidly 0.9 eq of Bromine (676.41 g) keeping the temperature below 3° C.

Note: Fast addition of the bromine reduce the level of impurity.

Stirred for 10 minutes between −3° C. and 3° C. and monitored by GC. (starting material (5.65 min): 18.6 AP; Desired bromide (7.32 min): 63.7 AP; Dibromide imp. (8.56 min): 1.35 AP; Cyclized acetophenone Imp. (5.34 min): 1.06 AP; Unknown Imp (7.21 min): 1.24 AP.

Notes

The five compounds mentioned above need to be follow closely during the reaction. The amount of starting ketone remaining should be below 4 AP by GC. If the reaction is pushed to be below 1 AP of starting material the amount of Dibromide impurity will increase.

To be sure to not over charge the bromine, the reagent was added by portion to avoid the formation at a high level of the dibromide impurity.

May have formation of solid during the reaction. The solid formed is the desired product. The solid will go into solution when the reaction is heated up after the quench. It may change the results of the GC for the amount of starting ketone remaining. If the level of Dibromide impurity with presence of solid in the reaction mixture is higher than 3 AP and the amount of starting material about 4-5 AP the reaction should be considered completed.

Added rapidly 0.2 eq of Bromine (150.31 g) keeping the temperature below 3° C.

Note: Fast addition of the bromine reduced the level of impurity.

Allowed to stir 10 min between −3° C. and 3° C. and monitored by GC (starting ketone (5.65 min): 3.7 AP; desired bromide (7.32 min): 77.4 AP; Dibromide imp. (8.56 min): 2.4 AP; Cyclized acetophenone Imp. (5.34 min): 2.3 AP; Unknown Imp (7.21 min): 1.0 AP.

The reaction was completed with a total of 1.1 eq of bromine.

Quench and Work-Up
Notes:
As soon as the reaction is completed the reaction mixture needs to be quenched into a solution of Potassium Carbonate to quench the HBr present in the reaction mixture. If the quench is not done rapidly, the impurity at 7.2 min will increase significantly.

The reaction mixture must be added to the potassium carbonate solution to avoid the formation of $CO_2$.

In a 22 L/3 neck round-bottomed flask was prepared a solution with Potassium Carbonate (649.98 g) with Water (3.00 kg).

Note: This solution must be prepared in advance.

The solution of potassium carbonate was cooled to 0-5° C.

Note: The solution must be pre-cooled to reduce the time before the quench.

The reaction mixture was transferred into the potassium carbonate solution under vacuum.

Note: The transfer is done in about 15-20 min. The quench is not very exothermic. Maximum temperature increase from 2° C. to 10° C. Solids may remain in the reactor, they don't need to be transferred into the quenched solution. They will dissolve when the reaction mixture is returned back into the reactor and with the increase of the temperature.

The quenched reaction mixture was returned back to the reactor.

Heated the reaction mixture up to 20-25° C. and stir 30 min at 20-25° C. A GC was done to see if there was any decomposition.

Starting ketone (5.65 min): 3.8 AP
Desired product (7.32 min): 76.6 AP
Dibromide imp. (8.56 min): 2.6 AP
Cyclized acetophenone Imp. (5.34 min): 3.0 AP
Unknown Imp (7.21 min): 1.1 AP Note: After 18 hrs of stirring at 15-25° C. no decomposition was seen on a small sample.

Stopped the stirring for phase split.
Notes:
Can see some rag in the aqueous layer but none of the desired product is present.
It takes about 20 min to obtain a clean phase split.
The pH of the Aqueous layer is 9.
Added Water (1.50 kg) and let it stir 15 min.
Stopped the stirring for the phase split.
Notes:
It takes about 15 min to obtain a clean phase split. The pH of the Aqueous layer is 8.
No desired product is present in the aqueous layer.
Added Sodium Chloride (half brine) (1.71 kg) and let it stir 15 min.
Stopped the stirring for the phase split.

Note: It took 15 min for a good phase split. The pH of the aqueous layer is 6-7.

A GC was done quantitatively after work-up to know the amount of desired product present in the Toluene solution.

Starting ketone (5.65 min): 3.8 AP
Desired product (7.32 min): 74.4 AP
Dibromide imp. (8.56 min): 2.5 AP
Cyclized acetophenone Imp. (5.34 min): 2.6 AP
Unknown Imp (7.21 min): 1.1 AP Note: The amount of bromide present: 1031 g.

Note: For the following steps the amounts were based on the amount of desired product obtained in the previous step above:

The solution was concentrated to (2 mL/g×1031 (the amount of desired product)+1031 (amount of desired product)=3093 mL.) with an evaporator at 40° C.

Note: The compound crystallized rapidly when the concentration is completed. The next step needs to be done quickly.

The concentrated solution of desired product was transferred into the 20 L reactor.

Note: The reactor jacket was pre-heated to 40° C. before the transfer of the solution.

Rapidly added Heptane (5.64 kg) keeping the temperature between 28-40° C.

Notes:
The stirring rate must be fast since dense orange-yellow solid will crystallize during the addition.
Small amount of seeds can be added if after 10% volume of the addition no crystallization occurs.
Cooled the slurry to 20-25° C. and let it stir overnight.

Note: No solid stuck on the side wall of the reactor.

A quantitative GC of the supernatant after overnight stirring was done.

Note: There was about 12-14% yield in the supernatant after overnight stirring.

The slurry was filtered and washed with 2×1 mL/g (based on the bromide amount from above) of heptane.

Dried under vacuum without heating to constant weight.

Note: The compound dries very fast.

Results:

Quantity: 825 g (60% yield not corrected).

Appearance: crystalline orange-yellow solid.

HPLC: 98.9 AP

GC: 99.6 AP

Example 7

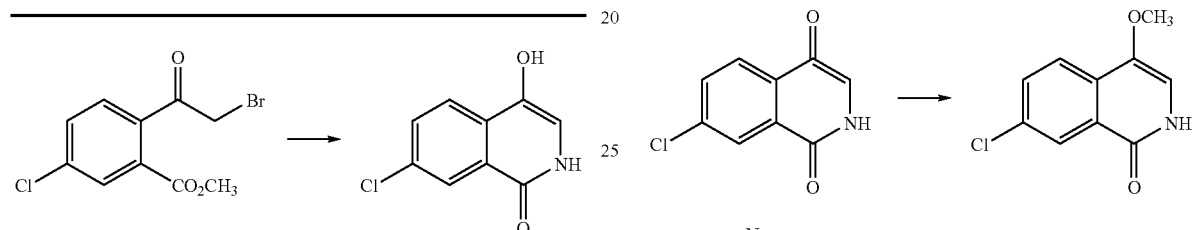

| Name | grams |
| --- | --- |
| Starting bromide | 10.00 |
| Sodium Diformylamide | 4.89 |
| Tetra-N-butylammonium Bromide | 1.11 |
| Acetonitrile | 62.66 |
| Tetrahydrofuran | 17.72 |
| Methanol | 23.75 |
| Water (quench system) | 100.00 |
| Methyl tert-butyl Ether (part of 50:50 wash) | 7.42 |
| Acetonitrile | 7.83 |
| Acetonitrile | 3.45 |
| Acetic Acid (quench system) | 1.26 |
| Water (cake wash) | 40.00 |
| Methanol (part of 50:50 MTBE:MeOH wash) | 7.92 |
| Methyl tert-butyl Ether (cake washes) | 37.08 |

Sodium Diformylamide was charged to reactor A and slurried in 1 ml acetonitrile/g-bulk LR (KF<0.05%) and 2 ml THF/g-bulk LR (KF<0.05%).

The slurry was cooled to 0° C.

In a separate flask, the starting bromide was dissolved in 5 ml acetonitrile/g-bulk LR (KF<0.05%) and then transferred to reactor A.

A clear solution of Tetra-N-butylammonium Bromide dissolved in 0.44 ml acetonitrile/g-bulk LR (KF<0.05%) was then added to the reaction mixture (reactor A) over ~15 minutes.

Post complete addition the reaction was warmed to ~15° C.

Note: the initial yellow/orange slurry slowly darkens as the reaction proceeds.

The reaction was aged with stirring @ 15-25° C. until complete conversion of the starting bromide (<0.5% LCAP).

Note: this usually requires approximately 10-12 hr.

Upon complete conversion of starting bromide to the diformylamide intermediate, 3 ml MeOH/g-bulk LR was added sub-surface over ~1 hr.

The reaction was then aged @ 20-25° C. for ~8-10 hrs.

Upon complete conversion of intermediate the reaction mixture was inversely quenched into a solution of Acetic acid (0.12 ml/g-bulk LR)/water (10 ml/g-bulk LR).

The quenched reaction mixture was stirred @ 20-25° C. for ~1 hr (final pH=4-5).

The slurry was then filtered.

The cake was then washed 2×2 ml $H_2O$/g-bulk LR.

The cake was then covered with a 50:50 MTBE/MeOH (2 ml/g-bulk LR) solution for ~30 min prior to applying vacuum.

The cake was then washed with 2 ml MTBE/g-bulk LR.

The cake was then washed 2×1.5 ml MTBE/g-bulk LR.

The solids were then dried on the filter pot via suction under a stream of nitrogen.

Upon drying a beige/brown solid was isolated in ~78% yield.

Example 8

| Name | grams |
| --- | --- |
| Starting alcohol | 483.60 |
| Methanesulfonic Acid | 2376.08 |
| Methanol | 2680.06 |
| Methanol | 197.92 |
| Ammonium Hydroxide | 3094.46 |
| Water | 5000.00 |

To a 12 L RBF (fitted with glycol-cooled condenser, gas inlet adaptor, stir bar and heating mantle) was added the starting alcohol (483.6 g) and Methanol (2.68 kg).

The slurry of brown solids was cooled to 3° C. in an ice/water bath.

Methanesulfonic Acid (2.38 kg) was added via addition funnel over about 25 minutes (VERY EXOTHERMIC). During the addition, the solids appeared to partially dissolve and the reaction mixture turned reddish brown.

The reaction mixture was heated to 60° C.

Heating was continued at 60° C. and the reaction monitored by HPLC.

HPLC results:

| Time (h) | SM (AP) | Product (AP) |
| --- | --- | --- |
| 2.5 | 86 | 13 |
| 24 | 14 | 84 |
| 46.5 | 3.7 | 95.1 |

After 47 hours, the reaction mixture was cooled to room temperature.

The mixture was filtered through diatomaceous earth (Celite®) to remove solids since the reverse quench was going to be done via addition funnel and residual solid could block the stopcock.

Ammonium Hydroxide (3.09 kg) was cooled using ice/water in a 22 L flask to 1.6° C.

The reaction mixture was added via dropping funnel to the ammonium hydroxide, keeping the temperature <30° C.

| Volume added (L) | Time | Temp (° C.) |
| --- | --- | --- |
| 0 | 12:01 | 1.6 |
| 1 | 12:11 | 22.3 |
| 3 | 12:38 | 27.0 |
| 4 | 12:48 | 28.3 |
| 5.1 | 13:03 | 25.4 |

The reaction flask was rinsed with 250 mL methanol to remove the remaining reaction mixture and the rinse transferred to the quench vessel.

The resulting slurry was held at room temperature. Quantitative samples of the supernatant taken after 1 hour, 3 hours, and 5 hours all showed the same level of product remaining in the mother liquors and the same impurity profile. In future, samples will be taken after cooling to room temperature and after 2 hours to determine whether or not the crystallization is complete.

The slurry was filtered through #54 Whatman paper, 24 cm diameter on a Buchner funnel.

The cake was washed with 5 L of water; each wash took about 10 minutes.

Cake dimensions before compression were 25 cm diameter, 5.5 cm thick for a volume of 2700 mL.

The solid was very slow to deliquor since the cake tends to crack very easily. The crystals are very fine and form a cake which does not release solvents easily.

The solid was dried under vacuum at 40° C. This took several days.

The desired product (466.2 g; 89.95% yield) was isolated. LOD of the solid was 0.46%. HPLC AP was 97.33 with 2.1 P starting material and 2 other unknown impurities.

Example 9

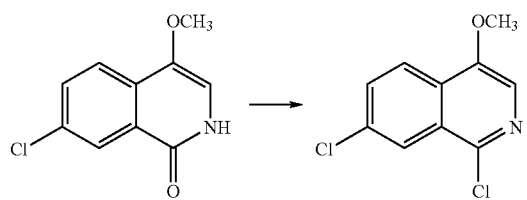

POCl$_3$ was added to a solution of starting 7-Cl-4-methoxy-isoquinolone in CH$_3$CN (13 L/kg) at 25° C. (Temperature Increase: ~4° C.). Reaction heated to reflux.

Checked conversion after 9 h by HPLC (250 nm): Conversion to desired product >99%. If not complete, reaction can be left for 16 h at reflux. If still not complete, 0.5 equiv. POCl$_3$ can be added and reaction can be checked for conversion after 2 h.

Decreased temperature to 25° C.

Transferred the reaction mixture slowly to a solution of K$_2$HPO$_4$ (18 wt %) (40 L/kg) equilibrated at 38° C. Controlled the addition, maximum temperature: 45° C. pH control: if <5 during the quench 5 L/kg of K$_2$HPO$_4$ added.

Stirred for 1 h at 38° C. after addition completed.

Added ethyl acetate: 30 L/kg and stirred for 30 min.

Phases were split: Aged for 15 minutes. At this stage: Vmax: 73 L/kg (Organic: 43 L/kg).

Corrective action: If inorganic salts present: added 10 L/kg water.

Corrective action: If rag layer present: added 10 L/kg ethyl acetate: Vmax: 83 L/kg (Vmax: 88 L/kg, Organic: 53 L/kg).

If both corrective are actions taken: Vmax: 103 L/kg (Organic: 53 L/kg).

Separated aqueous/organic phase. Checked for product in aqueous phase. <3% total yield. If failed, the aqueous phase would be extracted with 10 L/kg ethyl acetate, until the product had been extracted. Organic phase: 43 L/kg, if corrected: 53 L/kg, checked yield by HPLC calibration.

Added 10% weight/desired product of charcoal Darco G60. The charcoal was preliminarily stirred in ethyl acetate (5 L/kg).

Stirred at 25° C. for 2 h. Took a sample (1 ml), filtered, checked color and yield by HPLC. If solution was clear (visual estimation), the mixture was filtered. If not added 10% weight and left 2 h more. Same procedure. If not, added 10% more and left overnight.

Filtered on diatomaceous earth (Celite®) pad, washed with 20 L/kg of ethyl acetate. 68 L/kg<Vmax<78 L/kg.

Evaporated ethyl acetate and dried.

On a 10 g scale, the total yield was 75% (isolated material by selective crystallization; 63% yield; Potency: 102% (HPLC: RAP>99.9)).

What is claimed is:
1. A process for preparing a compound of formula (I)

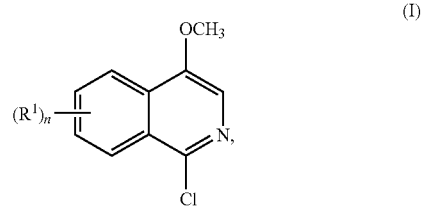

the process comprising:
(a) treating a compound of formula (A)

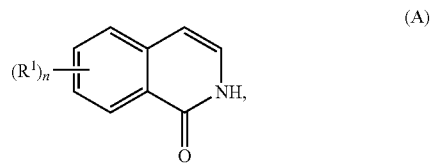

wherein
n is 0, 1, 2, 3, or 4; and
each R$^1$ is independently selected from alkoxy, alkyl, amino, aryl, cyano, halo, haloalkoxy, mercapto, and nitro;
with an anhydrous acid in the presence of methanol and a hypervalent iodine oxidizing agent; and
(b) treating the compound of step (a) with a chlorinating agent.

2. The process of claim 1 wherein
n is 1; and
R$^1$ is halo.

3. The process of claim 1 wherein the anhydrous acid of step (a) is methanesulfonic acid.

4. The process of claim 1 wherein the hypervalent iodine oxidizing agent is selected from phenyl iodine diacetate, bis (4-methylbenzenesulfonato-κO)phenyliodine, bis(2,2-dimethylpropanoato-κO)phenyliodine, phenylbis(trichloroacetato-O)iodine, bis(benzoato-κO)phenyliodine, phenylbis(2,2,-trifluoroacetateo-KO)iodine, and dichloroiodobenzene.

5. The process of claim 4 wherein the hypervalent iodine oxidizing agent is phenyl iodine diacetate.

6. The process of claim 1 wherein the chlorinating agent of step (b) is selected from POCl₃ and PCl₅.

7. The process of claim 6 wherein the chlorinating agent is POCl₃.

8. The process of claim 1 further comprising a process for preparing a compound of formula (A)

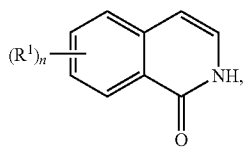
(A)

the process comprising:
(a) treating a compound of formula (B)

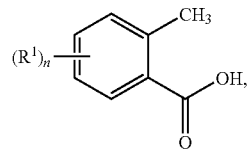
(B)

with oxalyl chloride and ammonium hydroxide;
(b) treating the product of step (a) with N,N-dimethylformamide dimethyl acetal; and
(c) treating the product of step (b) with a base.

9. The process of claim 8 wherein
n is 1; and
R¹ is halo.

10. The process of claim 8 wherein the base of step (c) is selected from potassium tert-butoxide, potassium tert-amylate, and potassium hexamethyldisilazide.

11. The process of claim 8 wherein the base is potassium tert-amylate.

12. The process of claim 8 wherein the process for preparing compound (A) is continuous.

* * * * *

UNITED STATES PATENT AND TRADEMARK OFFICE
CERTIFICATE OF CORRECTION

PATENT NO.         : 8,207,341 B2
APPLICATION NO.    : 12/547158
DATED              : June 26, 2012
INVENTOR(S)        : Shawn A. Springfield et al.

Page 1 of 1

It is certified that error appears in the above-identified patent and that said Letters Patent is hereby corrected as shown below:

On the Title page, Item (54), line 1, and in the Specification, Column 1, line 1, change "OR" to -- FOR --.

In the Specification:

Column 2, lines 47 and 48, change "phenylbis(2,2,2,-trifluoroacetateo-KO)iodine," to -- phenylbis(2,2,2,-trifluoroacetato-κO)iodine, --.

Column 5, line 37, change "phenylbis(2,2,2,-trifluoroacetateo-KO)iodine," to -- phenylbis(2,2,2,-trifluoroacetato-κO)iodine, --.

Column 8, lines 18 and 19, change "phenylbis(2,2,2,-trifluoroacetateo-KO)iodine," to -- phenylbis(2,2,2,-trifluoroacetato-κO)iodine, --.

In the Claims:

Claim 4:

Column 23, lines 1 and 2, change "phenylbis(2,2,2,-trifluoroacetateo-KO)iodine," to -- phenylbis(2,2,2,-trifluoroacetato-κO)iodine, --.

Signed and Sealed this
Eighth Day of April, 2014

Michelle K. Lee
*Deputy Director of the United States Patent and Trademark Office*